United States Patent
Greenstein (10) Patent No.: US 6,244,882 B1
(45) Date of Patent: Jun. 12, 2001

(54) MEDICAL CONNECTOR APPARATUS

(75) Inventor: Alan Greenstein, Seattle, WA (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 09/489,639

(22) Filed: Jan. 24, 2000

Related U.S. Application Data (63) Continuation of application No. 09/281,709, filed on Mar. 30, 1999, now Pat. No. 6,048,218, which is a continuation of application No. 08/561,527, filed on Nov. 21, 1995, now Pat. No. 5,967,817.

(51) Int. Cl.$^7$ ....................................................... H01R 4/60
(52) U.S. Cl. ........................... 439/205; 439/680; 439/909
(58) Field of Search ..................................... 439/680, 488, 439/490, 387, 732, 205, 909; 609/149–153

(56) References Cited

U.S. PATENT DOCUMENTS

| | | | |
|---|---|---|---|
| D. 242,720 | 12/1976 | Loforese | D26/1 B |
| D. 355,163 | 2/1995 | Dolson et al. | D13/133 |
| 1,157,026 | 10/1915 | Meschenmoser | 339/66 |
| 3,054,080 | 9/1962 | Jepson | 339/66 |
| 3,382,355 | 5/1968 | Prifogle et al. | 439/490 |
| 3,478,298 | 11/1969 | Nelson | 240/73 |

(List continued on next page.)

FOREIGN PATENT DOCUMENTS

| | | |
|---|---|---|
| 0052879 | 11/1981 | (EP) . |
| 6-196222 | 7/1994 | (JP) . |

*Primary Examiner*—Hien Vu (57) ABSTRACT

A medical connector apparatus that includes: (1) a first mating connector having a first conductive portion, (2) a second mating connector having a second conductive portion for electrically coupling to the first conductive portion, and (3) a housing unit with an interior chamber housing the second mating connector. In one embodiment of the invention, two apertures extend between the interior chamber and the housing unit's exterior. In another embodiment of the invention, the first mating connector further has a wiping portion for cleaning a portion of the second mating connector adjacent to the second conductive portion.

In still another embodiment of the invention, the housing chamber further has a light source positioned near the aperture through which the first mating member enters to electrically couple the first and second conductive portions. In this embodiment, the first mating connector has a light covering portion for covering the light source when the first and second conductive portions couple. The embodiments of the medical connector apparatus described above can serve as electrode connectors for all types of defibrillators.

16 Claims, 12 Drawing Sheets

U.S. PATENT DOCUMENTS

| | | | |
|---|---|---|---|
| 3,626,356 | 12/1971 | Trammell | 339/60 M |
| 3,654,586 | 4/1972 | Winkler | 339/49 R |
| 3,657,681 | 4/1972 | Falkner | 339/61 M |
| 3,760,332 | 9/1973 | Berkovits et al. | 439/843 |
| 3,824,524 | 7/1974 | Glover | 439/680 |
| 3,944,316 | 3/1976 | Newman et al. | 339/111 |
| 4,014,600 | 3/1977 | Gisewsky | 339/48 |
| 4,033,654 | 7/1977 | Ross | 439/843 |
| 4,299,431 | 11/1981 | Wilson et al. | 339/60 R |
| 4,386,818 | 6/1983 | Millhimes et al. | 439/490 |
| 4,403,824 | 9/1983 | Scott | 339/186 R |
| 4,413,872 | 11/1983 | Rudy et al. | 439/387 |
| 4,500,156 | 2/1985 | Nguyen | 339/94 C |
| 4,534,609 | 8/1985 | White | 339/117 R |
| 4,632,121 | 12/1986 | Johnson et al. | 128/639 |
| 4,671,597 | 6/1987 | Grill | 439/490 |
| 4,684,199 | 8/1987 | Ezure et al. | 439/610 |
| 4,762,388 | 8/1988 | Tanaka et al. | 350/96.2 |
| 4,764,129 | 8/1988 | Jones et al. | 439/677 |
| 4,772,219 | 9/1988 | Falchetti | 439/490 |
| 4,842,558 | 6/1989 | Strand | 439/490 |
| 5,035,644 | 7/1991 | Nakazato et al. | 439/372 |
| 5,145,417 | 9/1992 | Honkomp et al. | 439/685 |
| 5,356,304 | 10/1994 | Colleran | 439/205 |
| 5,520,547 | 5/1996 | Hamaoka et al. | 439/206 |
| 5,520,555 | 5/1996 | Taylor | 439/680 |
| 5,562,607 | 10/1996 | Gyory | 439/490 |
| 5,564,951 | 10/1996 | Attal et al. | 439/676 |
| 5,588,852 | 12/1996 | Puerner | 439/843 |
| 5,607,454 | 3/1997 | Cameron et al. | 607/5 |
| 5,879,374 | 3/1999 | Powers et al. | 607/5 |

MEDICAL CONNECTOR APPARATUS

This is a continuation of application Ser. No. 09/281,709 filed on Mar. 30, 1999, and now U.S. Pat. No. 6,048,218, and which is a cont. of Ser. No. 08/561,527, filed Nov. 21, 1995, and now U.S. Pat. No. 5,967,817.

The invention is directed towards a medical connector apparatus.

BACKGROUND OF THE INVENTION

Today, approximately three hundred and fifty thousand Americans die each year due to cardiac arrest. Eighty percent of these fatalities are due heart arrhythmia caused by ventricular fibrillation. Typically, ventricular fibrillation is treated by using a defibrillator to apply an electric shock to a patient's heart.

Three kinds of defibrillators are used by emergency medical personnel for applying a defibrillating shock to a patient suffering from cardiac arrest. These are: (1) manual defibrillators which charge and deliver shocks to patients solely in response to the user's request; (2) automatic defibrillators which charge and deliver shocks to patients solely in response to ECG data collected from the patient and analyzed by the defibrillator; and (3) semiautomatic defibrillators which analyze a patient's ECG data to advise on the delivery of shocks, but await shock delivery requests from their users before delivering defibrillating shocks.

Prior art defibrillators are quite complex and cumbersome. Consequently, in the past, defibrillators have usually been used only by emergency medical personnel with considerable training. Moreover, prior art defibrillators typically produce very low survival rates, because often quite a bit of time elapses before a trained medical operator (needed for applying the defibrillating shock) reaches the victim of cardiac arrest to apply a defibrillating shock. This poor response time greatly reduces the utility of the defibrillating shock since the chances of surviving a cardiac arrest exponentially decrease with time elapsed after the arrest.

Thus, in order to increase the utility of defibrillators, and thereby increase the number of lives saved, the defibrillator deployment time needs to be reduced. The defibrillator deployment time can be reduced by designing a defibrillator that can be used by non-medical personnel (such as police officers, fire fighters, teachers, supervisors, or common lay people) who can quickly reach victims of cardiac arrests in order to apply defibrillating shocks.

Such a defibrillator, that can be used by non-medical personnel, has to be light-weight and portable, so that it can be quickly carried to a victim of cardiac arrest. Moreover, the operation of this type of defibrillator has to be simple so that an inexperienced operator could easily use it to apply a defibrillating shock, even if the operator uses the equipment infrequently. Several such simple and portable defibrillators are disclosed in: U.S. patent application entitled "Defibrillator With Self-Test Features," filed on May 10, 1994, and having the Ser. No. 08/240,272; and U.S. patent application entitled "Electrotherapy Method and Apparatus," filed on Apr. 4, 1994, and having the Ser. No. 08/227,553. The disclosures of these patent applications are incorporated herein by reference.

One manner of simplifying the operation of a defibrillator (so as to allow a non-medical operator to easily use it) is to simplify the act of connecting an electrode pad cable to the defibrillator. A typical defibrillator has (1) an energy source that provides the motive power source for delivering a defibrillating shock; (2) an electrode connector that is housed in the defibrillator and that mates to the electrode connector of the electrode pad cable; and (3) a controller for actuating the defibrillator to deliver a defibrillation shock from the defibrillation energy source to the patient via the mated electrode connectors and electrode pads.

Non-medical personnel, who do not frequently operate defibrillators, may experience difficulties in connecting prior art electrode pad cables to prior art defibrillators, because these defibrillators do not provide sufficient guidance for rapidly establishing such connections. Consequently, there is a need in the art for a defibrillator connector apparatus that provides guidance for connecting the defibrillator connectors.

Moreover, the design of this defibrillator connector apparatus should minimize the effect of environmental residue on the operation of this apparatus. Environmental residue is material (such as blood, vomit, dirt, water, etc.) that exists in the environment in which the defibrillator is operated. While in storage or in standby mode, the connector apparatus of a defibrillator might accumulate residue, which would threaten the electrical or mechanical integrity of the connection during an emergency.

Alternatively, during actual use, residue may be unavoidably introduced into the connector apparatus, which would thereby result in the loss of precious time as the connectors would have to be cleaned or replaced. Consequently, there is a need in the art for a connector apparatus that enables residue to be easily and quickly removed from it during emergency and routine maintenance operations of the defibrillator. Ideally, the connector apparatus should clean itself when the connectors mate. In sum, there is a need in the art for a defibrillator connector apparatus that can be easily operated by non-medical personnel under all environmental conditions.

SUMMARY OF THE INVENTION

The invention is a medical connector apparatus that includes: (1) a first mating connector having a first conductive portion, (2) a second mating connector having a second conductive portion for electrically coupling to the first conductive portion, and (3) a housing unit with an interior chamber housing the second mating connector. In one embodiment of the invention, two apertures extend between the interior chamber and the housing unit's exterior. In another embodiment of the invention, the first mating connector further has a wiping portion for cleaning a portion of the second mating connector adjacent to the second conductive portion.

In still another embodiment of the invention, the housing chamber further has a light source positioned near the aperture through which the first mating member enters to electrically couple the first and second conductive portions. In this embodiment, the first mating connector has a light covering portion for covering the light source when the first and second conductive portions couple. The embodiments of the medical connector apparatus described above can serve as electrode connector apparatus for all types of defibrillators.

BRIEF DESCRIPTION OF THE DRAWINGS

The novel features of the invention are set forth in the appended claims. However, for purpose of explanation, several embodiment of the invention are set forth in the following figures.

DETAILED DESCRIPTION OF THE INVENTION

In the following description, numerous details are set forth for purpose of explanation. However, one of ordinary skill in the art would realize that the invention may be practiced without the use of these specific details. In other instances, well-known structures and devices are shown in block diagram form in order not to obscure the description of the invention with unnecessary detail.

The invention is a medical connector apparatus that includes: (1) a first mating connector having a first conductive portion, (2) a second mating connector having a second conductive portion for electrically coupling to the first conductive portion, and (3) a housing unit with an interior chamber housing the second mating connector. In one embodiment of the invention, two apertures extend between the interior chamber and the exterior of the housing unit. Through one aperture, the first mating connector is inserted into the interior chamber to electrically couple the first and second conductive portions.

Moreover, the second aperture is used as an outlet for environmental residue in the interior chamber. Specifically, when the first mating connector is inserted through the first aperture, environmental residue is forced out of the interior chamber through this second outlet, because of the depression force created by the insertion of the first mating connector. In addition, the existence of these two apertures facilitates the cleaning of the interior chamber.

In another embodiment of the invention, the first mating connector further has a wiping portion for cleaning a portion of the second mating connector adjacent to the second conductive portion. In turn, this cleaning enables a better connection to be established between the first and second conductive portions. This cleaning operation also improves the insulation between the conductive portions or between a conductive portion and an operator, by wiping away environmental residue that could establish an electrical path between the conductive portions or between a conductive portion and an operator.

In still another embodiment of the invention, the housing chamber further has a light source positioned near the aperture through which the first mating member enters to electrically couple the first and second conductive portions. In this embodiment, the first mating connector has a light covering portion for covering the light source when the first and second conductive portions couple. The embodiments of the medical connector apparatus described above can serve as electrode connectors for all types of defibrillators.

A. Pin and Socket Embodiment

Figure 1:
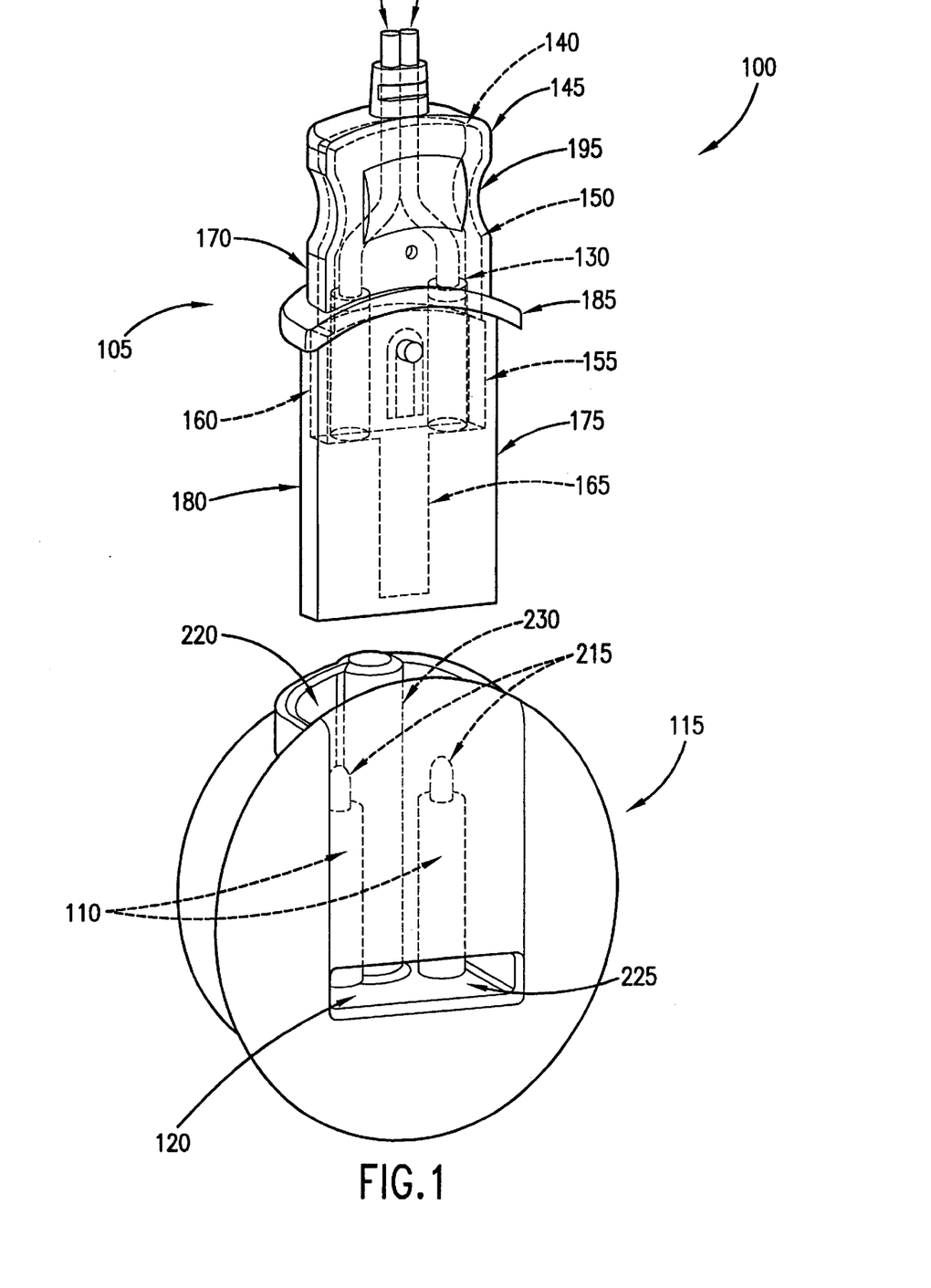
FIG. 1 presents one embodiment of the medical connector apparatus of the invention.

FIGS. 1–6 set forth one embodiment of the invention, which can be used as an electrode connector apparatus for all types of defibrillators. As shown in FIG. 1, medical connector apparatus 100 includes (1) a cable connector 105 having two conductive sockets, (2) a housed connector 110 having two conductive pins for coupling to the two conductive sockets, and (3) a housing unit 115 having an interior chamber 120 for housing connector 110.

1. Two Socket Cable Connector

Cable connector 105 includes two insulated electrical conductors 125, two conductive sockets 130, two silicone tubes 135, a rigid inner encasing shell 140, and an elastic outer encasing shell 145. When medical connector apparatus 100 is used as a defibrillator electrode connector apparatus, electrical conductors 125 connect to two electrode pads (not shown). In addition, as shown in FIG. 1, one end of each electrical conductor 125 connects to one of the two conductive sockets 130. Specifically, each conductive socket 130 is crimped onto the inner conductive wire of one of the two electrical conductors 125, in order to establish an electrical connection between the socket and the electrical conductor.

Figure 2:
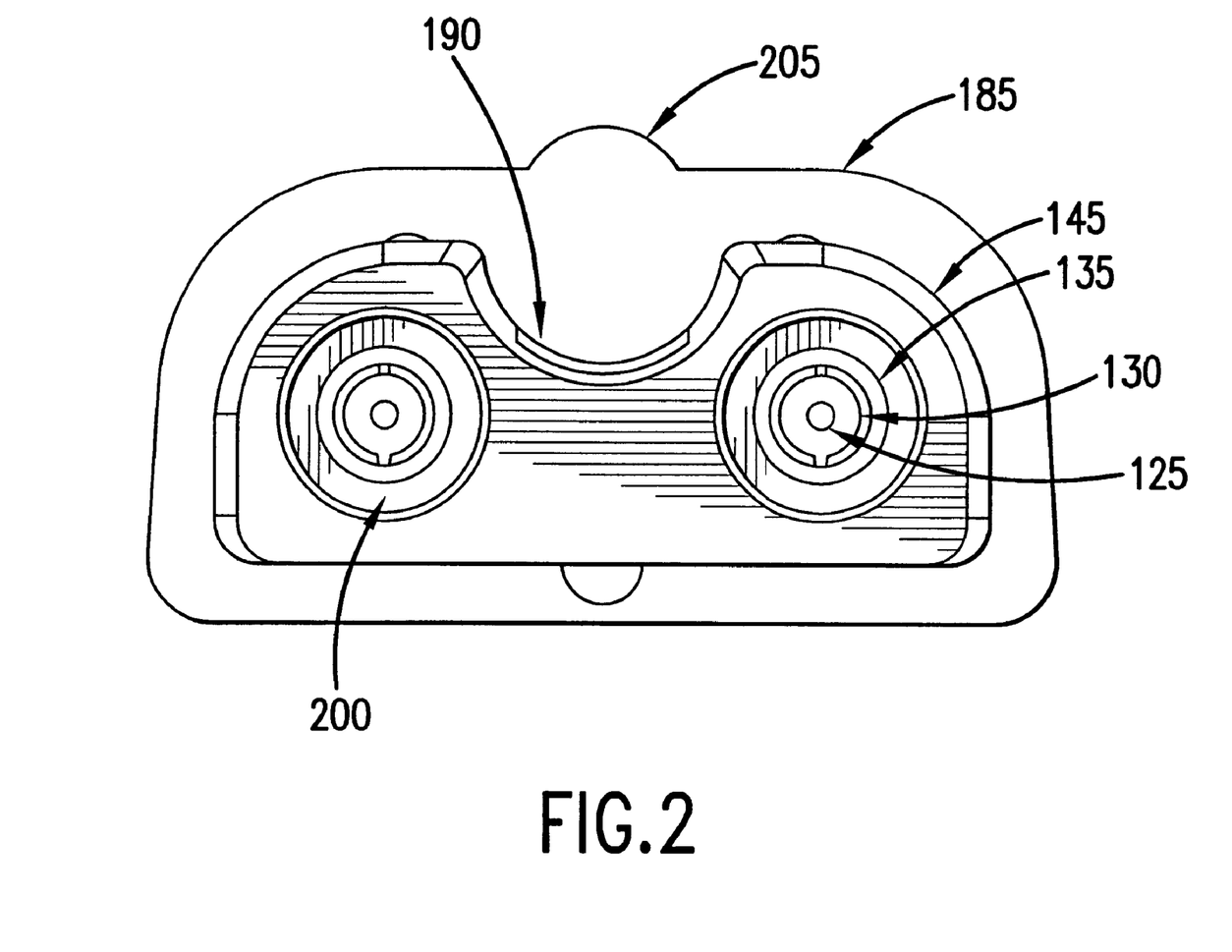
FIG. 2 presents a bottom side view of a cable connector of the medical connector apparatus of FIG. 1.
Figure 5:
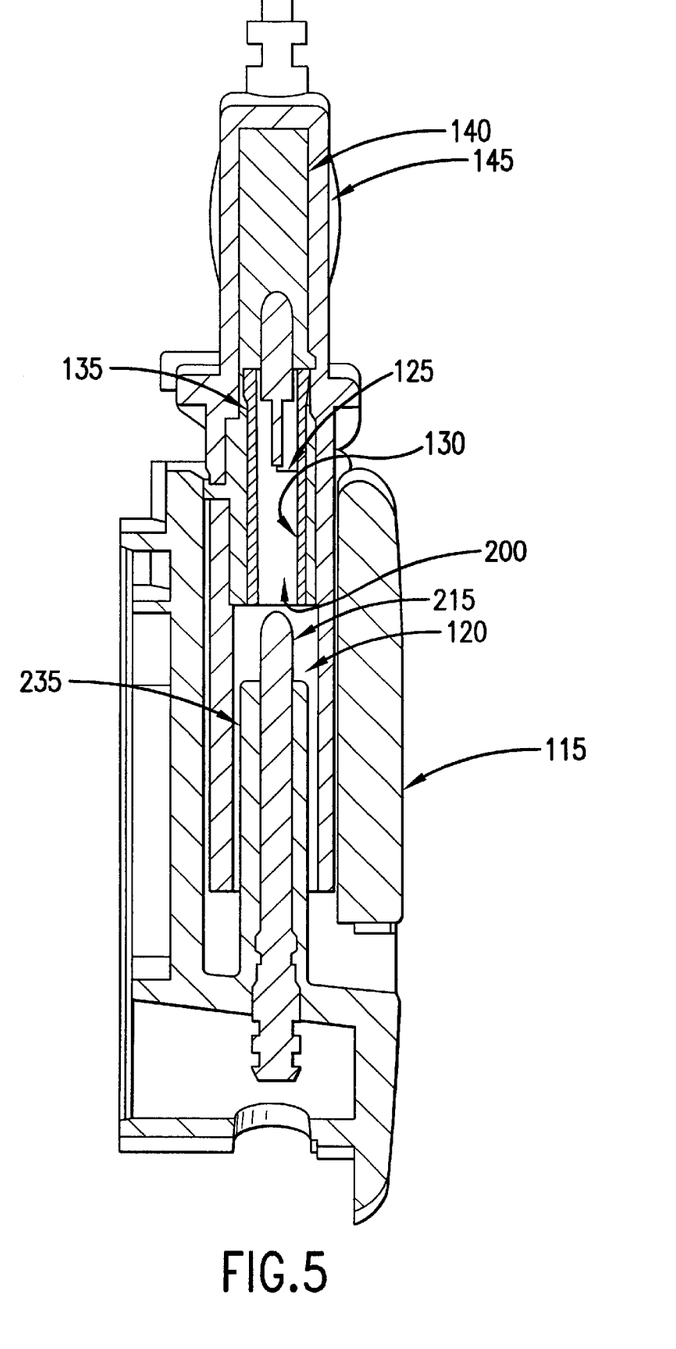
FIG. 5 presents a cross-sectional view, taken along section B—B of FIG. 4, of the cable connector partially inserted in the housing unit of FIG. 1, where section B—B runs through the center of a pin of a housed connector and a socket of the cable connector.

Moreover, as shown in FIGS. 2 and 5, each socket is then surrounded by a silicone tube 135. This silicone encasing provides a compressible cushion to allow the socket to expand over the mating portion, when the cable connector couples to the housed connector. In turn, silicone tubes 135, sockets 130, and the connector end of the electrical conductors are encased in rigid encasing shell 140.

This shell is a non-conductive polymer shell (such as a nylon or polyester shell) that is injection molded around the tubes, sockets, and conductors. This shell has three encasing portions 150, 155, and 160, and one supporting portion 165. As further shown in FIGS. 1 and 5, the first encasing portion is molded around the connector end of electrical conductors 125 and the crimped end of sockets 130. Each of the other two encasing portions encases a socket and its corresponding silicone tube. The three encasing portions insulate the two conductive paths (each of which is formed by an electrical conductor and a socket) from each other and from a user.

As further shown in FIG. 1, rigid encasing shell 140 also includes supporting portion 165, which extends downwardly from the second and third encasing portions. This supporting portion serves as a rigid support for the center of elastic encasing shell 145, which is molded around the rigid encasing shell 140. Elastic shell 145 has three encasing portions 170, 175, and 180, a flange 185, and a channel 190. The elastic shell's first encasing portion 170 surrounds first encasing portion 150 of rigid shell 140. As shown in FIG. 1, encasing portion 170 has inward bends 195 for enabling a user to grip and hold cable connector 105.

In addition, elastic shell 145 includes second and third encasing portions 175 and 180, which respectively surround second and third encasing portions 155 and 160. Moreover, as shown in FIGS. 1, 2, and 5, second and third encasing portions 175 and 180 extend downwardly below second and third encasing portions 155 and 160 to define two chambers 200. Each of these chambers is axially aligned with one socket and its corresponding silicone tube, so that, when the cable connector is inserted into the interior chamber of the housing unit, a pin projects through the chamber to reach its corresponding socket.

Furthermore, channel 190 is defined on the front side of elastic shell 145 between second encasing portion 175 and third encasing portion 180. This channel (which is supported by supporting portion 165) prevents the second and third encasing portions 175 and 180 from loosely hanging off the end of second and third encasing portions 155 and 160. In addition, as further discussed below, a light pipe housed in housing unit 115 slides on this channel when cable connector 105 is inserted into the interior chamber of the housing unit.

Elastic shell 145 further includes flange 185 between first encasing portion 170 and second and third encasing portions 175 and 180. As shown in FIG. 2, on the front side of elastic shell 145, flange 185 has a protruding semi-circular element 205. This element, along with the portion of the flange that is adjacent to it, covers a light pipe housed in housing unit 115, when cable connector 105 is inserted into the interior chamber of the housing unit.

In one embodiment of the invention, elastic shell 145 is a non-conductive thermoplastic elastomer, whose elasticity is between 40 to 90 durometers on the Shore A scale. This elasticity improves the durability of cable connector 105. In addition, the elastic nature of the walls of chambers 200 facilitates the removal of environmental residue from these chambers.

Figure 2A:
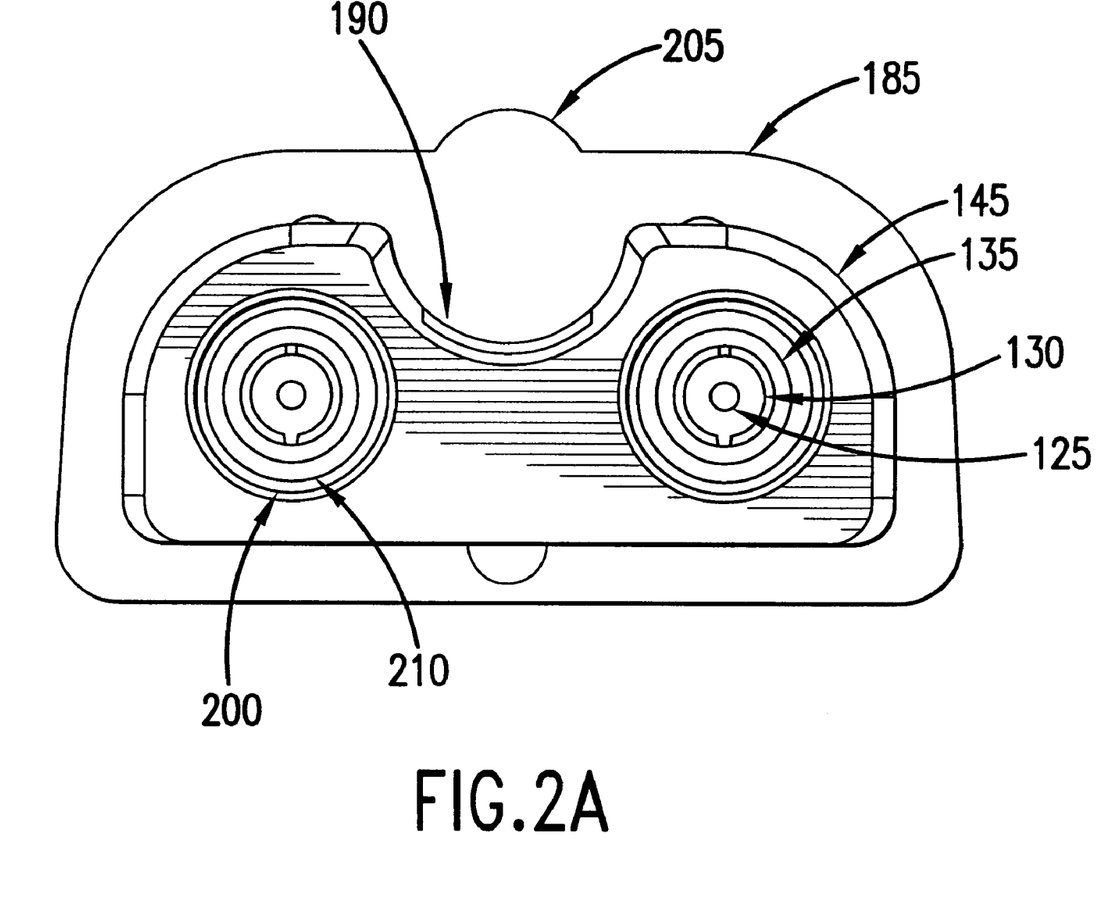
FIG. 2A presents a bottom side view of another cable connector of the medical connector apparatus of FIG. 1.

Finally, since elastic shell 145 is molded onto rigid shell 140, flexible plastic wiping rings can be easily produced in each chamber 200, during the molding. FIG. 2A sets forth one embodiment of these wiping rings 210. Each ring, in turn, provides a wiping action which cleans the surrounding insulating column of the pin that projects through the ring's chamber, when the cable connector is inserted into the interior chamber.

2. The Housing Unit and Housed Pin Connectors

Medical connector apparatus 100 also includes a housing unit 115 that houses, in an interior chamber 120, a housed connector 110. As shown in FIGS. 1 and 5, housed connector 110 includes two conductive pins 215, which extend vertically upwards from the bottom end of the interior chamber. The housed connector also includes two insulating columns 235, each of which surrounds a pin so as to leave only a portion of the pin exposed.

Housing unit 115 also has two apertures that extend between interior chamber 120 and the exterior of the housing unit. First aperture 220 is formed on the top side of housing unit 115. Through this aperture, cable connector 105 is inserted into the interior chamber to couple the sockets and the pins.

Figure 3:
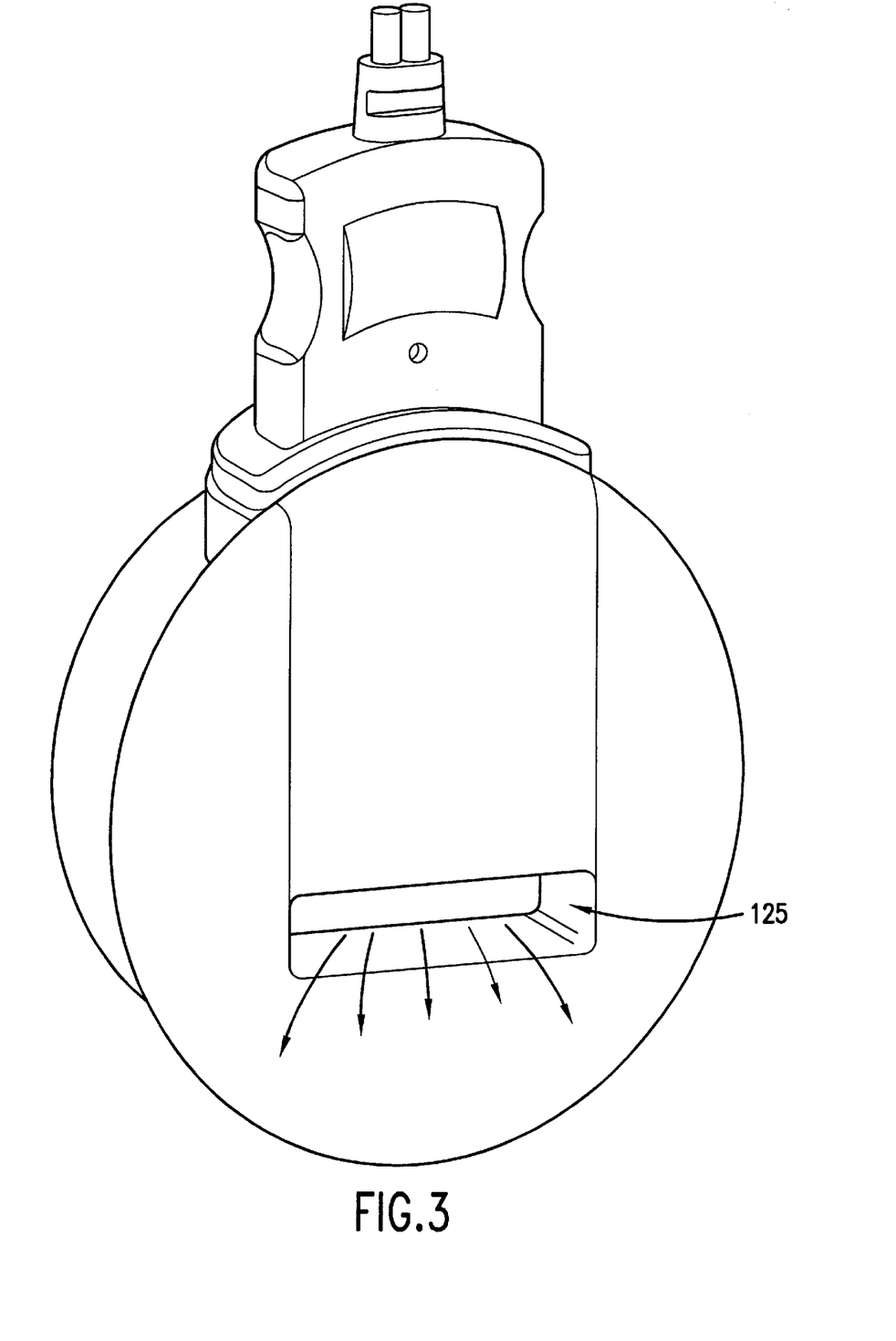
FIG. 3 presents a perspective view of the cable connector of FIG. 2 inserted in a housing unit of the medical connector apparatus of FIG. 1.
Figure 4:
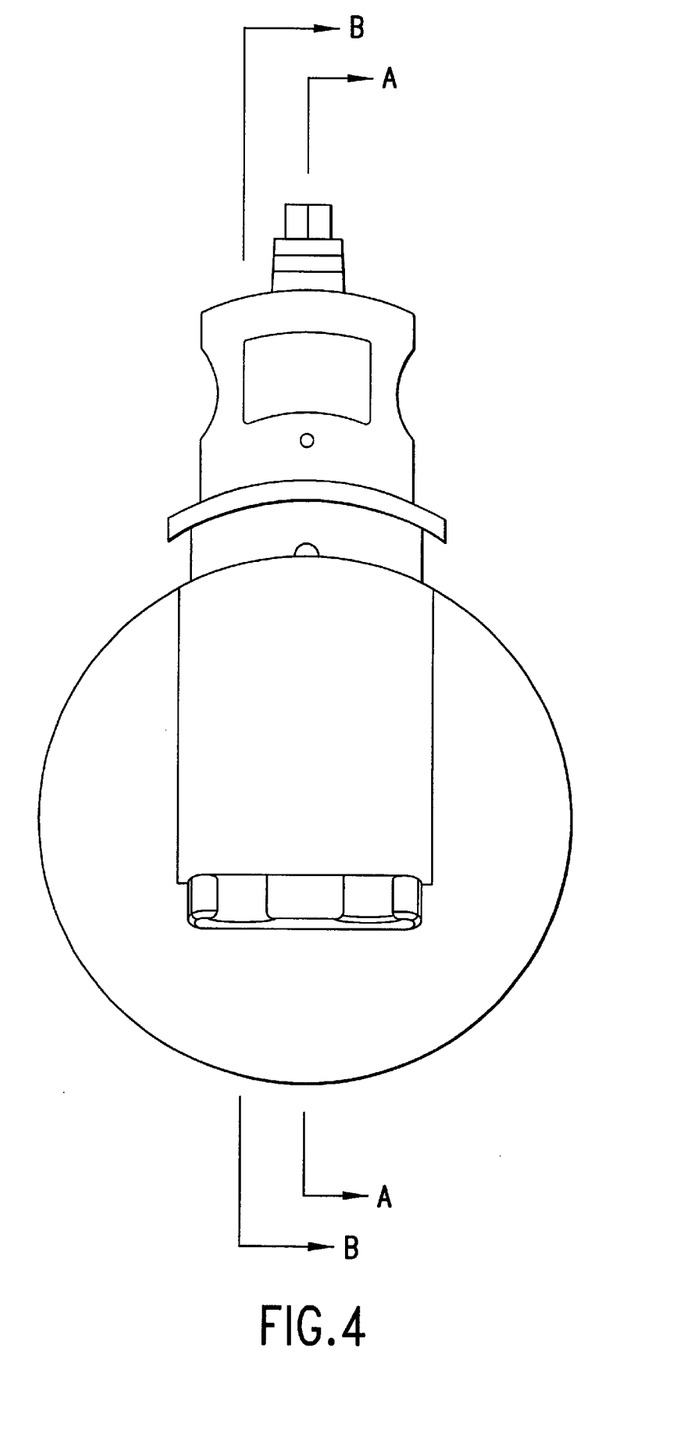
FIG. 4 presents a back side view of the cable connector of FIG. 2 inserted in a housing unit of the medical connector apparatus of FIG. 1.

Second aperture 225, on the other hand, is formed on the lower back side of the housing unit. As shown in FIG. 3, this second aperture serves as an outlet for environmental residue in the interior chamber. Specifically, when the cable connector is inserted through the first aperture, environmental residue is forced out of the interior chamber through this second outlet, because of the depression force created by the insertion of the cable connector.

In addition, the existence of these two apertures facilitates the cleaning of the interior chamber. In particular, this additional aperture allows an easy access for cleaning swabs, and provides an outlet for flushing fluids used during routine cleaning and maintenance operations. The two apertures are arranged such that liquids cannot accumulate in the housing unit. In other words, irrespective of the orientation of the housing unit, liquids (such as blood, vomit, rain, etc.) may drain out of the interior chamber through one of the outlets.

On its front side, housing unit 115 includes a light pipe 230, which extends vertically upward from the bottom end of the interior chamber. An LED is embedded in this light pipe. This LED is used to direct the operator to insert the cable connector into the interior chamber, during the operation of the medical device (e.g., the defibrillator) to which medical connector apparatus 100 is attached. The operator's attention may be directed to the light at the appropriate time by other displays on the medical device and/or by voice prompts from the device. The light may also blink or flash to attract the operator's attention.

As mentioned before, the semi-circular, light covering portion 205 of flange 185 covers this light pipe, when pins 215 enter sockets 130. In other words, the LED and its corresponding pipe are also used to inform an operator that an electrical connection has been established between pins 215 and sockets 130. When properly inserted, light covering portion 205 fully obscures the top of the light pipe to signal the completion of the connector insertion to the operator.

Figure 6:
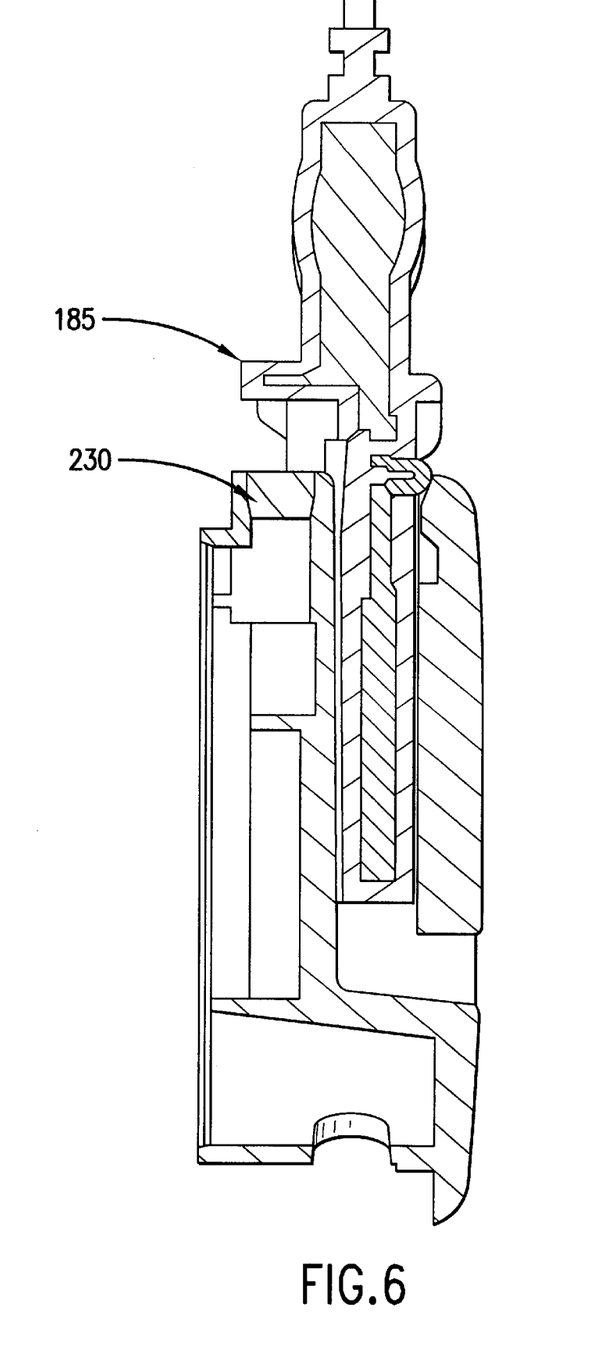
FIG. 6 presents a cross-sectional view, taken along section A—A of FIG. 4, of the cable connector partially inserted in the housing unit of FIG. 1, where section A—A runs through a plane of symmetry of the cable connector and the housing unit.

As shown in FIGS. 1, 5, and 6, the inner recess of interior chamber 120 and the outer elastic shell of cable connector 105 are molded in a complementary fashion. In particular, as shown in FIG. 1, the bends on the corners of the front side of interior chamber 120 provide two channels for supporting the curved front side of encasing portions 175 and 180. In addition, channel 190 of cable connector 105 provides a complementary surface to the cylindrical outer surface of light pipe 230. Also, the backside of both outer elastic shell 145 and interior chamber 120 are flat.

In one embodiment of the invention, housing unit 115 is part of (i.e., is encased in) a medical device. In this embodiment of the invention, conductors pass through the bottom of this housing unit to connect each housed conductive pin 215 to a power source of the medical device. In a more specific embodiment of the invention, housing unit 115 is part of (i.e., is encased in) a defibrillator. Some examples of such a defibrillator are disclosed in: U.S. patent application entitled "Defibrillator With Self-Test Features," filed on May 10, 1994, and having the Ser. No. 08/240,272; and U.S. patent application entitled "Electrotherapy Method and Apparatus," filed on Apr. 4, 1994, and having the Ser. No. 08/227,553. In this embodiment of the invention, conductors pass through the housing unit to connect housed conductive pins 215 to the power source of the defibrillator.

B. Coupling Ring Embodiment

Figure 7:
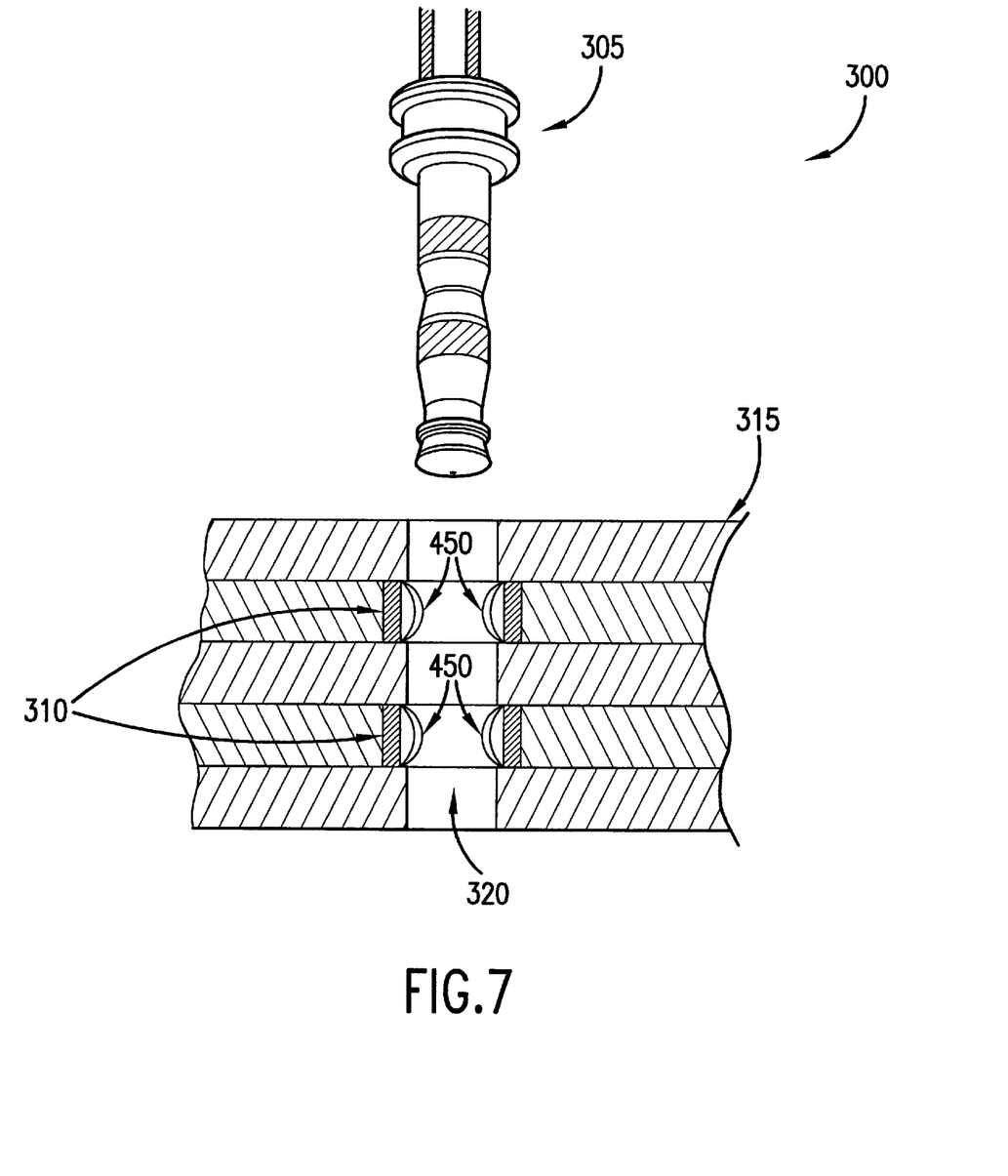
FIG. 7 presents another embodiment of the medical connector apparatus of the invention.

FIGS. 7–11 set forth another embodiment of the invention, which can be used as an electrode connector apparatus for all types of defibrillators. As shown in FIG. 7, medical connector apparatus 300 includes (1) a cable connector 305 having two conductive rings, (2) a housed connector 310 having two conductive rings for electrically coupling to the two rings of the cable connector, and (3) a housing unit 315 having an interior chamber 320 for housing connector 310.

1. Single Column Cable Connector

Figure 8:
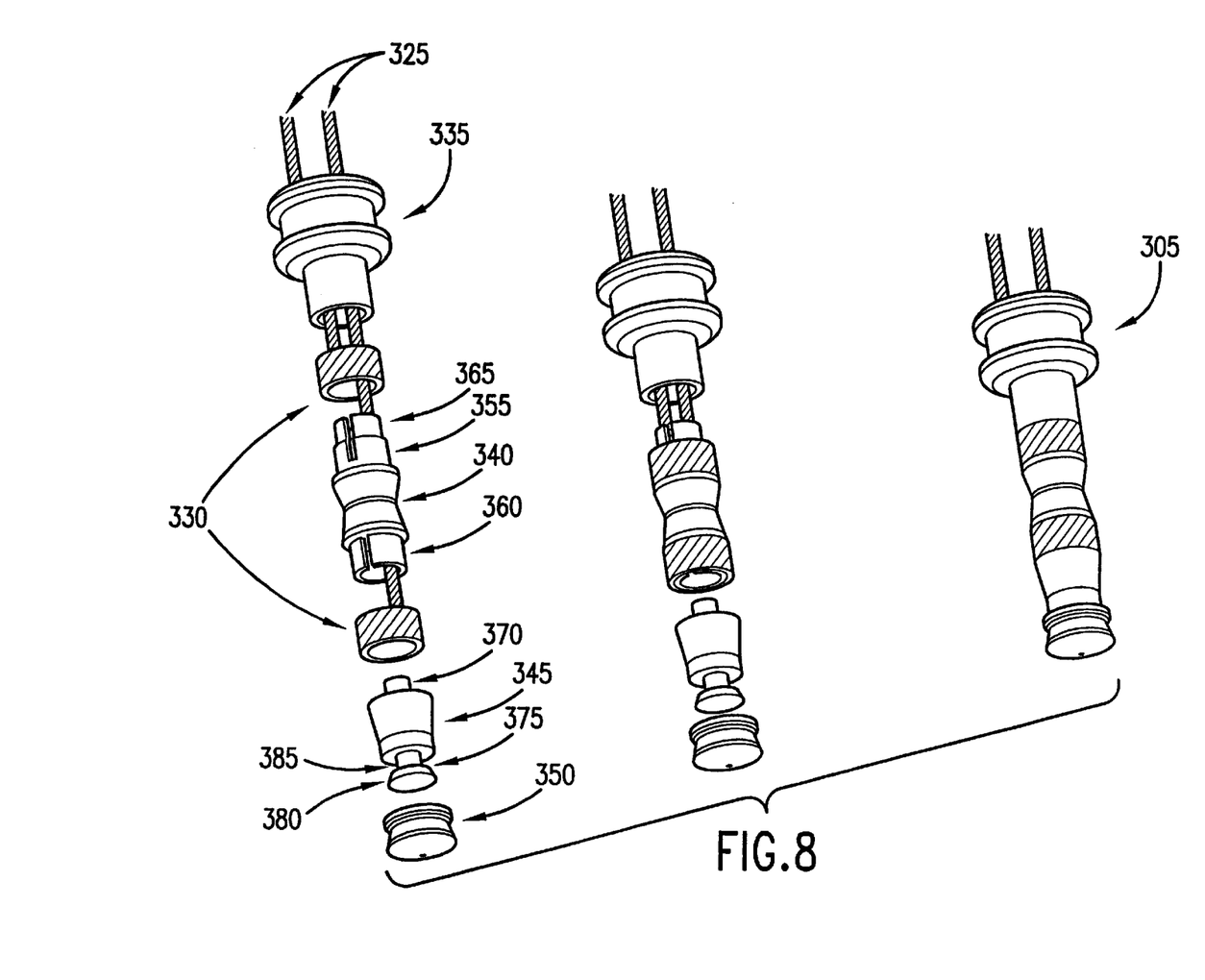
FIG. 8 presents a cable connector of the medical connector apparatus of FIG. 7.

FIG. 8 sets forth one embodiment of cable connector 305. This cable connector is configured to have an exterior surface that is complementary to the inner recess of interior chamber 320 of housing unit 315, so that, when this cable connector is inserted in the interior chamber, its two conductive rings electrically couple to the two conductive rings of the housed connector. As shown in FIG. 8, this connector includes two insulated electrical conductors 325, two conductive rings 330, a top insulating member 335, a middle insulating member 340, a bottom insulating member 345, and a wiping member 350.

When medical connector apparatus 300 is used as a defibrillator electrode connector apparatus, electrical conductors 325 connect to two electrode pads (not shown). In addition, as shown in FIG. 8, one end of each electrical conductor 325 connects to one of the two conductive rings 330. For example, the inner conductive wires of electrical conductors 325 are soldered to conductive rings 330, in order to establish an electrical connection between the rings and the electrical conductors.

As further shown in FIG. 8, conductive rings 330 then slide on hollow hubs 355 and 360, which extend from both ends of middle insulating member 340. This hollow middle member also includes hollow hub 365, which extends vertically from the top end of middle insulating member 340. Hub 365 is concentric with hub 355, but has a smaller diameter than this hub. Moreover, hub 365 is inserted in the hollow bottom end of top insulating member 335 in order to couple the top and middle members.

Furthermore, middle insulating member 340 connects to lower insulating member 345 by inserting plug 370 of the lower member into the cavity at the center of hub 360. Lower insulating member 345 also connects to wiping member 350 by inserting post 375 of the lower member into an open end of wiping member 350. The open end of wiping member 350 is made of a resilient material that (1) allows this end to expand when head 380 of inserting post 375 enters the cavity at the wiping member's center, and then (2) causes this end to contract towards neck 385 of inserting post 375 to prevent head 380 from exiting the cavity.

The wiping member provides a wiping action which cleans interior chamber 320, and thereby cleans housed connector 310, when the cable connector is inserted into the interior chamber. In addition, each of the insulating members 335, 340, and 345 is made of a plastic, such as thermoplastic polyester. These three insulating portions insulate the two conductive paths, each of which is formed by an electrical conductor 325 and a conductive ring 330. For insulation purposes, insulating member 340 is half an inch long, in one embodiment of the invention.

2. The Housing Unit and Housed Ring Connectors

Figure 9:
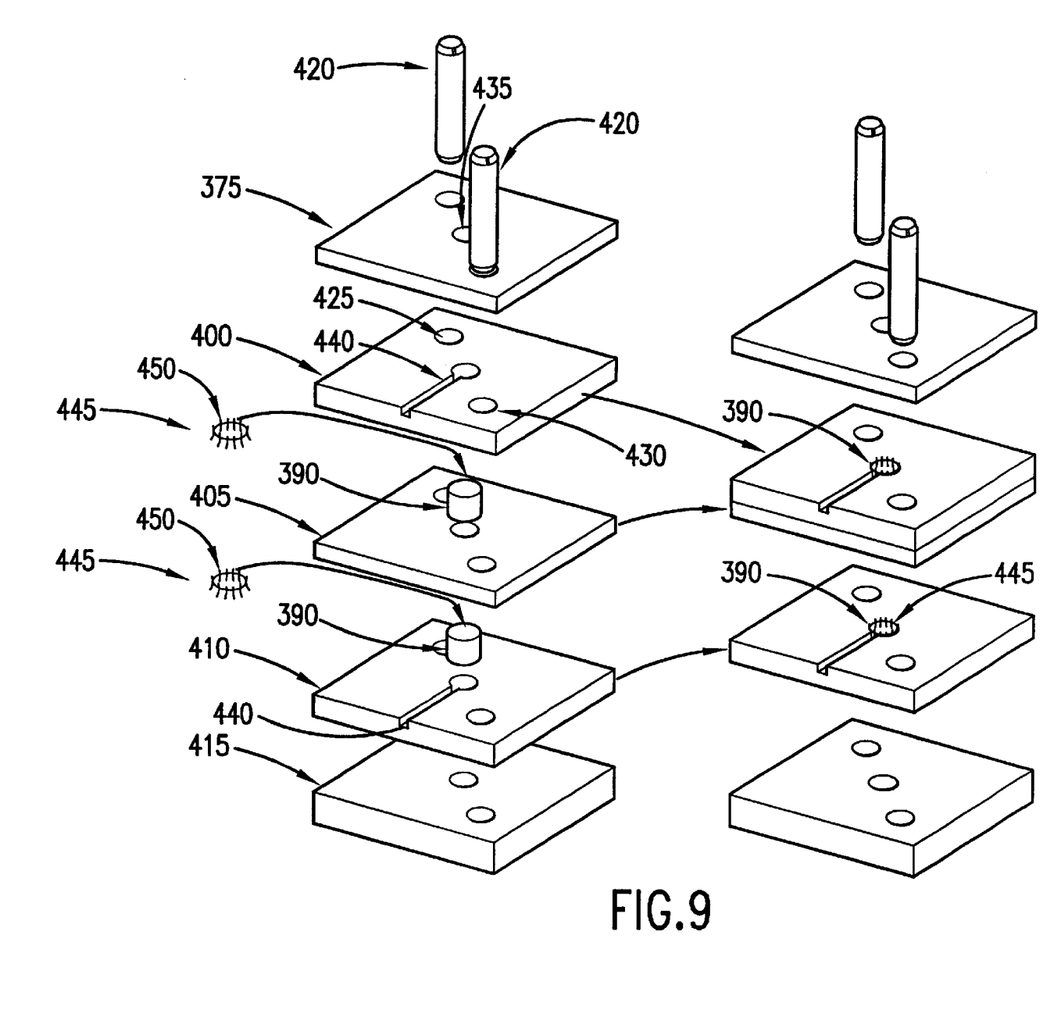
FIG. 9 presents a sectional view of a housing unit and a housed connector of the medical connector apparatus of FIG. 7.
Figure 10:
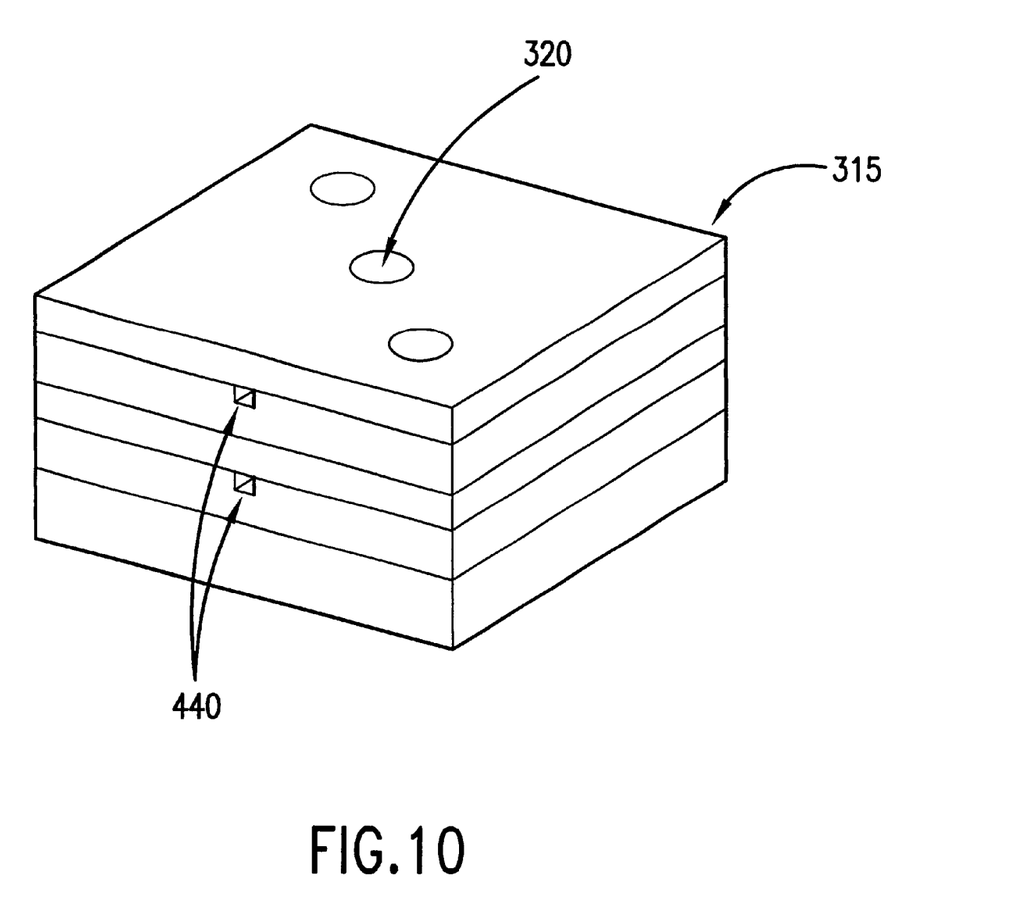
FIG. 10 presents a perspective view of the housing unit of the medical connector apparatus of FIG. 7.

Medical connector apparatus 300 also includes a housing unit 315 that houses, in an interior chamber 320, a housed connector 310. As shown in FIGS. 7 and 9, housed connector 310 includes (1) two conductive rings 390, which are individually housed in two separated, insulting plates, so that only the inner portion of each ring is exposed in interior chamber 320, and (2) two resilient contact members 445 coupled to the interior surfaces of rings 390.

More specifically, as shown in FIGS. 7 and 9, housing unit 315 includes five insulating plates 395, 400, 405, 410, 415, two coupling pins 420, two conductive rings 390, and two resilient contact members 445. In addition, each insulating plate has three apertures 425, 430, and 435. As set forth in FIG. 9, coupling pins 420 are inserted through all apertures 425 and 430, in order to connect all five insulating plates in the manner shown in FIGS. 9 and 10. In one embodiment of the invention, the insulating plates are made of a thermoplastic material, such as polyester or polycarbonate.

By stacking all five insulating plates, their apertures 435 collectively form the housing unit's interior chamber 320, into which single column cable connector 305 is inserted. In other words, apertures 435 of the first and fifth insulating plates 395 and 415 serve as two apertures that extend between interior chamber 320 and the exterior of the housing unit.

In turn, cable connector 305 is inserted into the interior chamber through aperture 435 of first insulating plate 395, in order to electrically couple the conductive rings. Aperture 435 of the fifth insulating plate 415, on the other hand, serves as an outlet for environmental residue from the interior chamber. Specifically, when the cable connector is inserted through the top aperture 435, environmental residue is forced out of the interior chamber through this outlet, because of the depression force created by the insertion of the cable connector.

As mentioned before, the existence of two apertures also facilitates the cleaning of the interior chamber. In particular, the additional aperture allows an easy access for cleaning swabs, and allows an outlet for flushing fluids used during routine cleaning and maintenance operations. Furthermore, the two apertures are arranged such that liquids cannot accumulate in the housing unit. In other words, irrespective of the orientation of the housing unit, liquids (such as blood, vomit, rain, etc.) drain out of the interior chamber through one of the outlets.

As further shown in FIG. 9, second and fourth insulating plates 400 and 410 house the two conductive rings 390. These two conductive rings are insulated (1) from each other by third insulating plate 405, and (2) from the environment outside of interior chamber 320 (e.g., from an operator or a patient) by first and fifth insulating plates 395 and 415. For insulation purposes, the first, third, and fifth insulating plates are half an inch thick, in one embodiment of the invention.

Both the second and fourth insulating plates also have a channel 440 defined on them. One conductor passes through each channel to connect on one of its ends to the exterior of a conductive ring, and to connect on its other end to a power source of the medical device. As shown in FIGS. 7 and 9, each hollow ring 390 also connects at its interior surface to a conductive, resilient contact member 445. A resilient contact member includes a number of individual resilient contact arcs 450 which are interconnected. One example of such a resilient contact member is sold under the brand name Louvertac bands by AMP, Inc.

Figure 11:
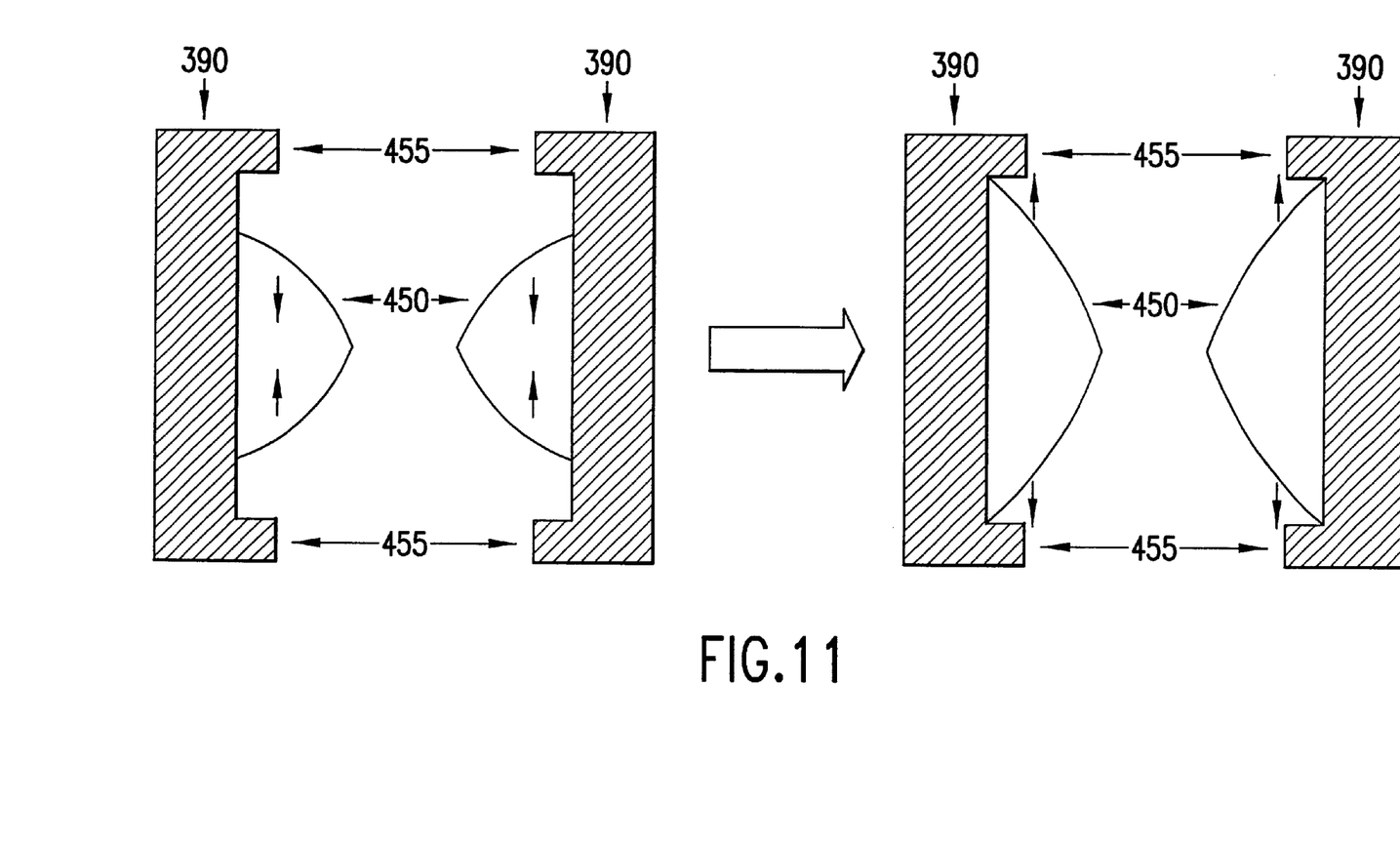
FIG. 11 presents a cross sectional view of a coupling between a housed conductive ring and resilient contact arcs of the housed connector of FIG. 9.

As shown in FIG. 11, in one embodiment of the invention, a resilient contact member 445 couples to the interior surface of hollow ring 390 by inserting the two ends of each of its resilient contact arc 450 between two lips 455 that are formed on the top and bottom surface of hollow ring 390. After these ends are inserted between the two lips, the resilient nature of arcs 450 cause them to expand to engage the inner surface of the lips, which creates the frictional force necessary for coupling contact member 445 to hollow ring 390.

Resilient contact members 445 establish the electrical coupling between the two housed conductive rings 390 and the two cable connector conductive rings 330. Specifically, when cable connector 305 is inserted into interior chamber 320, connector conductive rings 330 contact resilient contact members 445. These resilient contact members then bend towards rings 390, and thereby create space for conductive rings 330. In addition, as these contact members are conductive, and as these members are connected at their ends to housed rings 390, contact members 445 electrically couple the housed and connector rings.

In one embodiment of the invention, housing unit 315 is part of (i.e., is encased in) a medical device. In a more specific embodiment of the invention, housing unit 315 is part of (i.e., is encased in) a defibrillator. Some examples of such a defibrillator are disclosed in: U.S. patent application entitled "Defibrillator With Self-Test Features," filed on May 10, 1994, and having the Ser. No. 08/240,272; and U.S. patent application entitled "Electrotherapy Method and Apparatus," filed on Apr. 4, 1994, and having the Ser. No. 08/227,553. In this embodiment of the invention, the conductors, that pass through channels 440 of second and fourth plates 400 and 410, connect housed conductive rings 390 to the power source of the defibrillator.

While the invention has been described with reference to numerous specific details, one of ordinary skill in the art would recognize that the invention can be embodied in other specific forms without departing from the spirit of the invention. For instance, although the invention has been described by reference to mating connectors that each have one or two mating conductive portions, one of ordinary skill in the art would realize that an alternative embodiment of the invention has mating connectors that each have more than two mating conductive portions.

In addition, although medical connector apparatus 100 has been described to have an interior chamber housing both housed pins, one of ordinary skill in the art would recognize that an alternative embodiment of this apparatus has two interior chambers, with each housing one conductive pin. Furthermore, one of ordinary skill in the art would appreciate that an alternative embodiment of medical connector apparatus 300 has a housed light source that is covered by a light covering portion of cable connector 305, when its conductive rings electrically couple with the housed conductive rings.

Also, one of ordinary skill in the art would understand that, for one embodiment of medical connector apparatus 300, the housing unit is not formed by stacking five discrete insulating plates, but rather is integrally molded as a single insulating unit with the conductive rings and connecting conductors. This integral unit is then mounted inside a medical device housing by using sealing means such as O-rings. Moreover, one of ordinary skill in the art would appreciate that, although the invention has been described by reference to conductors 125 and 325 which are insulated wires, alternative embodiments of the invention utilize alternative conductors, such as flexible circuits. Therefore, one of ordinary skill in the art would understand that the invention is not to be limited by the foregoing illustrative details, but rather is to be defined by the appended claims.

We claim:

1. An electrical medical connector apparatus, comprising:
   a housing unit having,
      an interior chamber,
      a semi-cylindrical portion having a semi-cylindrical surface extending into the interior chamber,
      a housed electrical connector comprising two conductive sleeves disposed in a single column and electrically insulated from each other by an insulating member, and
      a front end having a first aperture to receive a cable connector having a semi-cylindrical portion;
      a backside;
      a second aperture formed on the backside and connected with the interior chamber to provide an outlet for environmental residue within the interior chamber when the cable connector is inserted into the first aperture to make an electrical connection with the housing unit; and
   the cable connector inserted into the first aperture and comprising two electrical conductors each electrically connected to a respective conductive sleeve of the housed electrical connector.

2. The electrical medical connector apparatus of claim 1 wherein the housing unit further comprises a bottom wall including a second aperture connecting with the interior chamber to provide an outlet for environmental residue within the interior chamber when the cable connector is inserted into the first aperture to make an electrical connection with the housing unit.

3. The electrical medical connector apparatus of claim 1 wherein the cable connector further comprises a socket including two conductive rings electrically insulated from each other by an insulating member, each conductive ring electrically connected to a respective electrical conductor.

4. The electrical medical connector apparatus of claim 3 further comprising an expandable tube surrounding the socket, the expandable tube expanding when the socket makes electrical connection with the housed electrical connector.

5. The electrical medical connector apparatus of claim 1 wherein the cable connector further comprises a wiping ring to provide a wiping action to the housed electrical connector.

6. The electrical medical connector apparatus of claim 1 wherein the semi-cylindrical portion of the cable connector further comprises a semi-cylindrical channel formed in the exterior of the cable connector, the semi-cylindrical channel adapted to slide over the semi-cylindrical surface of the semi-cylindrical portion of the housing unit when the cable connector is inserted in the housing unit.

7. The electrical medical connector apparatus of claim 1 wherein:
   the semi-cylindrical portion of the housing unit comprises an opening; and
   the cable connector further comprises a light-covering portion that covers the opening of the semi-cylindrical portion of the housing unit when the cable connector is inserted in the housing unit.

8. An electrical medical cable connector comprising:
   a shell;
   two electrical conductors each electrically connected to a respective conductive ring, the conductive rings electrically insulated from each other by an insulating member and disposed in a single socket within the shell;
   a semi-cylindrical surface formed in the shell to slide over a semi-cylindrical surface of a housing unit into which the cable connector is inserted to make electrical contact between the cable connector and the housing unit; and
   a wiping ring to provide a wiping action to an electrical connector of the housing unit into which the cable connector is inserted to make electrical contact between the cable connector and the housing unit.

9. The electrical medical cable connector of claim 8 further comprising an expandable tube in the shell surrounding the socket.

10. The electrical medical cable connector of claim 8 further comprising a light-covering portion extending over the channel to cover a light disposed within the channel when the cable connector is inserted in the housing unit to make electrical contact between the cable connector and the housing unit.

11. An electrical medical connector apparatus comprising:
   a housing unit and an electrical medical cable connector, the housing unit having, an interior chamber, the housing unit forming a semi-cylindrical surface extending into the interior chamber, a housed electrical connector comprising two conductive sleeves electrically insulated from each other by an insulating member, and a front end having an aperture for receiving the electrical medical cable connector; and wherein the electrical medical cable connector comprises, two electrical conductors each electrically connected to a respective conductive ring, the conductive rings electrically insulated from each other and located in a socket within a shell of the electrical medical cable connector, a semi-cylindrical channel formed in the shell to slide over the semi-cylindrical surface of the housing unit when the cable connector is inserted in the aperture to make electrical contact between the cable connector and the housing unit, an expandable tube in the shell surrounding the socket, and a wiping ring to wipe the housed electrical connector when the cable connector is inserted in the aperture.

12. The electrical medical connector apparatus of claim 11 wherein the housing unit is formed from a rigid material and the cable connector is formed from a pliable material.

13. An electrical medical connector apparatus comprising:

a housing unit and an electrical medical cable connector, the housing unit having, an interior chamber, the housing unit forming a semi-cylindrical surface extending into the interior chamber, a housed electrical connector comprising two conductive sleeves electrically insulated from each other by an insulating member, a front end having a first aperture for receiving the electrical medical cable connector, a bottom wall, and a second aperture connecting with the interior chamber to provide an outlet for environmental residue; and wherein the electrical medical cable connector comprises, two electrical conductors each electrically connected to a respective conductive ring, the conductive rings electrically insulated from each other and located in a socket within a shell of the electrical medical cable connector, a semi-cylindrical channel formed in the shell to slide over the semi-cylindrical surface of the housing unit when the cable connector is inserted into the first aperture to make an electrical connection with the housing unit, and a wiping ring to wipe the housed electrical connector when the cable connector is inserted in the first aperture.

14. The electrical medical connector apparatus of claim 13 wherein the housing unit is formed from a rigid material and the cable connector is formed from a pliable material.

15. A medical connector apparatus comprising:

a female mating connector having a semi-cylindrical interior chamber housing with an electrical connector therein comprising two conductive sleeves electrically insulated from each other by an insulating member, each sleeve formed from a respective ring contact located on a respective end of the insulating member, and a light pipe having a light therein extending along the interior chamber, wherein the interior chamber of the female mating connector slidably receives a male mating connector having a socket including two conductive ring electrically insulated from each other by an insulating member, each conductive ring for receiving a corresponding sleeve of the female mating connector; and wherein the female mating connector is formed of a material of greater rigidity than the male mating connector.

16. The medical connector apparatus of claim 15 wherein the male mating connector further comprises an expandable tube surrounding the socket, the expandable tube expanding when the socket makes electrical connection with the female mating connector.

* * * * *